(12) United States Patent
Ganey et al.

(10) Patent No.: US 11,160,904 B2
(45) Date of Patent: *Nov. 2, 2021

(54) BIOLOGICAL COMPOSITION IN A PROTECTANT SHROUD AND METHODS

(71) Applicant: Vivex Biologics Group, Inc., Atlanta, GA (US)

(72) Inventors: Timothy Ganey, Tampa, FL (US); Shabnam Namin, Miami, FL (US); Renaud Sicard, Miami, FL (US); Wendy W. Weston, Miami, FL (US)

(73) Assignee: Vivex Biologies Group, Inc., Atlanta, GA (US)

( * ) Notice: Subject to any disclaimer, the term of this patent is extended or adjusted under 35 U.S.C. 154(b) by 34 days.

This patent is subject to a terminal disclaimer.

(21) Appl. No.: 15/837,694

(22) Filed: Dec. 11, 2017

(65) Prior Publication Data

US 2018/0326122 A1 Nov. 15, 2018

Related U.S. Application Data

(63) Continuation-in-part of application No. 15/591,513, filed on May 10, 2017, now Pat. No. 10,513,690, and a continuation-in-part of application No. 15/590,444, filed on May 9, 2017, and a continuation-in-part of application No. 15/590,475, filed on May 9, 2017, now Pat. No. 10,760,058.

(51) Int. Cl.
*A61L 27/54* (2006.01)
*A61L 27/36* (2006.01)
*A61L 27/50* (2006.01)
*A61L 27/58* (2006.01)

(52) U.S. Cl.
CPC .......... *A61L 27/3687* (2013.01); *A61L 27/36* (2013.01); *A61L 27/3608* (2013.01); *A61L 27/3683* (2013.01); *A61L 27/3691* (2013.01); *A61L 27/505* (2013.01); *A61L 27/54* (2013.01); *A61L 27/58* (2013.01); *A61L 2300/604* (2013.01); *A61L 2300/62* (2013.01); *A61L 2300/802* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 2,622,027 | A | 12/1952 | Torr |
| 5,837,539 | A | 11/1998 | Caplan et al. |
| 9,192,695 | B2 | 11/2015 | Shi |
| 2005/0013872 | A1 | 1/2005 | Freyman |
| 2007/0191963 | A1 | 8/2007 | Winterbottom et al. |
| 2010/0105132 | A1 | 4/2010 | Totey et al. |
| 2012/0093885 | A1* | 4/2012 | Sahoo ........................ A61P 7/02 424/400 |
| 2013/0071358 | A1 | 3/2013 | Peterson |
| 2014/0065240 | A1* | 3/2014 | Mitsialis ................ A61K 35/28 424/577 |
| 2016/0030639 | A1 | 2/2016 | Shi |

FOREIGN PATENT DOCUMENTS

| | | |
|---|---|---|
| WO | 2014159662 | 10/2014 |
| WO | 2015016761 | 2/2015 |

OTHER PUBLICATIONS

Matsumura et al., Cell Transplantation, vol. 19, pp. 691-699, 2010.*
Matsumura et al., Journal of Biomaterials Science, Polymer Edition, 2013, vol. 24, No. 12, pp. 1484-1497.*
Weston et al., BioDrugs (2019) 33: 137-158.*
Capela et al., Thesis, 2006, School of Molecular Sciences, Victoria University, Werribee Campus, 158 pages (Year: 2006).*
Tarleton et al., Stabilization Methods for Textiles from Wet Sites—Abstract, Journal of Field Archaeology, vol. 22, No. 1 (1995), pp. 81-95 (Year: 1995).*
Zhang et al., Biomed & Biotechnol, 2010, vol. 11, No. 11, pp. 889-894 (Year: 2010).*
Bone Structure and Function; ASBMR educational materials; https://depts.washington.edu/bonebio/ASBMRed/structure.html.
Cells and Organelles; http://biology.cld.uc.edu/courses/bio104/cells.htm.
Derivative definition; Merriam Webster; http://www.merriam-webster.com/dictionary/derivative.
E.Linetsky, N.Kenyon, H.Li, X.Xu and C.Ricordi; Increased Immunogenicity of Human Vertebral Body Marrow After Processing in Bovine Versus Human Serum Albumin; Elsevier Science Inc.; Transplantation Proceedings 29, 1960 (1997).

(Continued)

*Primary Examiner* — Scott Long
*Assistant Examiner* — Evelyn Y Pyla
(74) *Attorney, Agent, or Firm* — David L. King

(57) ABSTRACT

A biological composition intermixed with a polyampholyte protectant for direct implantation has a mixture of biologic material and a volume of polyampholyte protectant. The mixture of biologic material has non-whole cellular components including vesicular components and active and inactive components of biological activity, cell fragments, cellular excretions, cellular derivatives, and extracellular components, or whole cells or combinations of the non-whole cellular components and whole cells, wherein the mixture is compatible with biologic function. The volume of polyampholyte protectant is intermixed with the mixture of biologic material, wherein the polyampholyte protectant is a liquid of a polyamine polymer compound of carboxylated poly-lysine and wherein the polyampholyte protectant forms a three-dimensional bonding shroud externally enveloping each of the non-whole cellular components, if any, and each of the whole cells, if any, of the mixture of biologic material.

36 Claims, 12 Drawing Sheets
(11 of 12 Drawing Sheet(s) Filed in Color)

(56) References Cited

OTHER PUBLICATIONS

Matsumura, Kazuaki; Hyon, Suong-Hyu; Polampholytes as low toxic efficient cryoprotective agents with antifreeze protein properties; Biomaterials 30, 2009, 4842-4849.

Nottestad, Sheri Y.; Baumel, Julian J.; Kimmel, Donald B.; Recker, Robert R. and Heany, Robert P; The Proportion of Trabecular Bone in Human Vertebrae; Journal of Bone and Mineral Research, vol. 2, No. 3 1987.

Oryan et al.; Bone regenerative medicine: classic options, novel strategies, and future directions, Journal of Orthopaedic Surgery and Research, 2014, vol. 9:18, pp. 1-27.

Brockbank et al., Advances in Biopreservation, 2006, pp. 157-196; retrieved from the internet; www.andrew.cmu.edu/user/yr25/TaylorPublications/MJTaylor108.pdf.

* cited by examiner

Polyampholyte cryoprotectant    DMSO-based cryoprotectant

BIOLOGICAL COMPOSITION IN A PROTECTANT SHROUD AND METHODS

RELATED APPLICATIONS

The present application is a continuation in part of applications U.S. Ser. No. 15/591,513 entitled, "Biologic Composition And Method Of Manufacture" filed on May 10, 2017; and U.S. Ser. No. 15/590,444 entitled, "Acellular Biologic Composition And Method Of Manufacture" filed on May 9, 2017; and U.S. Ser. No. 15/590,475 entitled, "Acellular Biologic Composition And Method Of Manufacture" filed on May 9, 2017.

TECHNICAL FIELD

This invention is a tissue regenerative biologic composition. More specifically, a composition at least in part formed from bone marrow and a method of manufacture and use of said composition with an acellular mixture.

BACKGROUND OF THE INVENTION

In the area of tissue regeneration or repair, the use of stem cell therapy has been widely touted.

Often, these inventions describe isolating the stem cells, purifying and culturally expanding mesenchymal stem cells. In U.S. Pat. No. 5,837,539, entitled "Monoclonal Antibodies For Human Mesenchymal Stem Cells", Arnold Caplan et al. reported that the cells are preferably culturally expanded, but suggest it is possible to use the stem cells without culture expansion. Caplan also describes a way to isolate stem cells.

A major technological hurdle to producing a safe allogeneic composition with viable cells has been the need to approach a fraction of risk approaching zero by removing all antigenic properties that lead to inflammation factors in a separation to yield only a certain stromal cell type. This has proven difficult in practice, as the in-process access degrades the quantity of viable cells that can be effectively harvested.

The present invention has yielded a biological composition that is safe and achieves favorable patient outcomes after direct implantation and does so in a method that allows a resultant mixture of biologic material to be recovered from human cadaver tissue such as bone marrow wherein the mixture unexpectedly exhibits evidence of viability independent of whole cells such as mesenchymal cells in the dose while sustaining a legacy or memory of the lineages from where the acellular biological composition came which retains the ability to support the emergence of new tissue forms including bone and other tissues. The mixture can include whole cells in combination with the acellular material or can be primarily whole cell based. The mixture is coated in a protectant suitable for direct implantation.

These and other benefits of the present invention and the method of preparing it are described hereinafter.

SUMMARY OF THE INVENTION

A biological composition intermixed with a polyampholyte protectant for direct implantation has a mixture of biologic material and a volume of polyampholyte protectant. The mixture of biologic material has non-whole cellular components including vesicular components and active and inactive components of biological activity, cell fragments, cellular excretions, cellular derivatives, and extracellular components, or whole cells or combinations of the non-whole cellular components and whole cells, wherein the mixture is compatible with biologic function. The volume of polyampholyte protectant is intermixed with the mixture of biologic material, wherein the polyampholyte protectant is a liquid of a polyamine polymer compound of carboxylated poly-lysine and wherein the polyampholyte protectant forms a three-dimensional bonding shroud externally enveloping each of the non-whole cellular components, if any, and each of the whole cells, if any, of the mixture of biologic material.

The bonding shroud deters attachment to other cells for a predetermine time. The bonding shroud also buffers inflammation and further can retard or reduce premature differentiation of the whole cells of the mixture. The bonding shroud also sustains regenerative potential and biologic function of the mixture during preservation and implantation. The bonding shroud is configured to be metabolized after implantation after a predetermined time, the predetermined time can be three or more days, preferably the predetermined time is up to six days. The three-dimensional bonding shroud forms a spherical shell about each whole cell. Preferably, the polyampholyte protectant is a cryoprotectant.

The polyampholyte protectant forms a strong hydrophilic characteristic of the bonding shroud to protect the cell membrane external of the whole cells. The protectant when frozen as a cryoprotectant interrupts crack propagation externally protecting the cell membrane.

In one embodiment, the biological composition has a mixture of mechanically selected biologic material derived from bone marrow. The mixture has non-whole cellular components including vesicular components and active and inactive components of biological activity, cell fragments, cellular excretions, cellular derivatives, and extracellular components. The mixture including non-whole cell fractions including one or more of exosomes, transcriptosomes, proteasomes, membrane rafts, lipid rafts might what in sum is a secretome vestment of biological potential. The mixture is compatible with biologic function.

The mixture of mechanically selected material derived from bone marrow. The biological composition preferably has bone particles. The bone particles can be added to the mixture derived from bone marrow. The bone particles include a mixture of cortical bone particles and cancellous bone particles.

The combination of non-whole cell components with a select number of non-whole cell fractions sustains pluripotency in the cells. In a preferred embodiment, the biological composition is predisposed to demonstrate or support elaboration of active volume or spatial geometry consistent in morphology with that of endogenous bone. The biological composition extends regenerative resonance that complements or mimics tissue complexity. The mixture is treated in a protectant or cryoprotectant prior to preservation or cryopreservation or freeze drying. The composition can be maintained at ambient temperature prior to freeze drying. The protectant or cryoprotectant creates a physical or electrical or chemical gradient or combination thereof for tissue regeneration. The gradient can have a physical characteristic of modulus or topography, such as charge density, field shape or cyto-, cryo or chemo taxic tendencies. The gradient can have a chemical characteristic of spatially changing compositions of density or species of functional molecules, wherein the molecules can offer a fixed catalytic function as a co-factor. Also, the gradient can have an electrical characteristic of charge based or pH-based or electron affinities that confer metastability in biologic potential.

The bone marrow mixture which is derived from a cadaver has separation-enhanced non-whole cell fractions imbuing vitality including one or more of the following:

separating the fractions from cells heightens their vitality, reversing "arrest" of donors, responsive molecular coupling, matrix quest in neutralizing inflammation or satience by balancing stimulus for repair. The protectant or cryoprotectant is a polyampholyte. The regenerative resonance occurs in the presence or absence of a refractory response. When using a cryoprotectant, the cryopreservation occurs at a temperature that is sub-freezing wherein the cryopreservation temperature is from 0 degrees C. to −200 degrees C. The protection may also be achieved by non-cryogenic means.

The biological composition's non-whole cellular component also can include organelle fragments and the active and inactive components of biological activity which can also include extants of the human metabolome.

A method of making a biological composition of the present invention has the steps of: collecting, recovering and processing bone marrow from a cadaver donor; mechanically separating the cellular or non-cellular components or a combination thereof of bone marrow from cadaverous bone; concentrating by centrifugation and filtering; separation by density gradient centrifugation; collecting non-cellular fractions or non-cellular components or a combination thereof of predetermined density; washing the non-whole cellular fractions or non-cellular components or a combination thereof to create the mixture; quantifying concentrations of non-cellular fractions components at a non-zero entity; suspending to a predetermined concentration in a polyampholyte cryoprotectant; freezing the mixture at a predetermined controlled rate; and packaging a bone blend having particles in the size range of 100 to 300 μm of demineralized cortical bone, mineralized cortical bone and mineralized cancellous bone either within the mixture or separate. These particle size ranges can vary higher or lower depending on the application. At the time of use, the mixture is thawed by immersion in a warm water bath for 2-3 minutes at 37 degrees C. It is diluted in saline without spinning; and then the diluted mixture, with or without the bone blend being intermixed, can be implanted by packing, injection, scaffolding or any other suitable means into a patient.

Definitions

DNase—deoxyribonuclease is any enzyme that catalyzes the hydrolytic cleavage of phosphodiester linkages in the DNA backbone, thus degrading DNA.

DMEM, DMEM/LG—Dulbecco's Modified Eagle Medium, low glucose. Sterile, with: Low Glucose (1 g/L), Sodium Pyruvate; without: L-glutamine, HEPES (4-(2-hydroxyethyl)-1-piperazineethanesulfonic acid)

Dimethyl sulfoxide (DMSO) is an organosulfur compound with the formula (CH3)2SO. This colorless liquid is an important polar aprotic solvent that dissolves both polar and nonpolar compounds and is miscible in a wide range of organic solvents as well as water. It has a relatively high melting point.

DPBS—Dulbecco's Phosphate Buffered Saline.

CBT-MIXER—Mixing blade for Cancellous Bone Tumbler Jar.

Chimera—A genetic chimerism or chimera (also spelled chimaera) is a single organism composed of cells with distinct genotypes.

Cold Media—Media used during the preparation of vertebral bodies for initial processing.

Cryopreserved—Tissue frozen with the addition of, or in a solution containing, a cryoprotectant agent such as glycerol, or dimethylsulfoxide, or carboxylated poly-1-lysine.

Freeze Dried/Lyophilized—Tissue dehydrated for storage by conversion of the water content of frozen tissue to a gaseous state under vacuum that extracts moisture.

Normal Saline—0.9% Sodium Chloride Solution.

Packing Media—Media used during initial processing and storage of the processed vertebral bodies prior to bone decellularization.

PBS—Phosphate Buffered Saline.

Processing Media—Media used during bone decellularization that may contain DMEM/Low Glucose no phenol red, Human Serum Albumin, Heparin, Gentamicin and DNAse.

BRIEF DESCRIPTION OF THE DRAWINGS

The patent or application file contains at least one drawing/photograph executed in color. Copies of this patent or patent application publication with color drawing(s) will be provided by the Office upon request and payment of the necessary fee.

The invention will be described by way of example and with reference to the accompanying drawings in which.

DETAILED DESCRIPTION OF THE INVENTION

Figure 1:
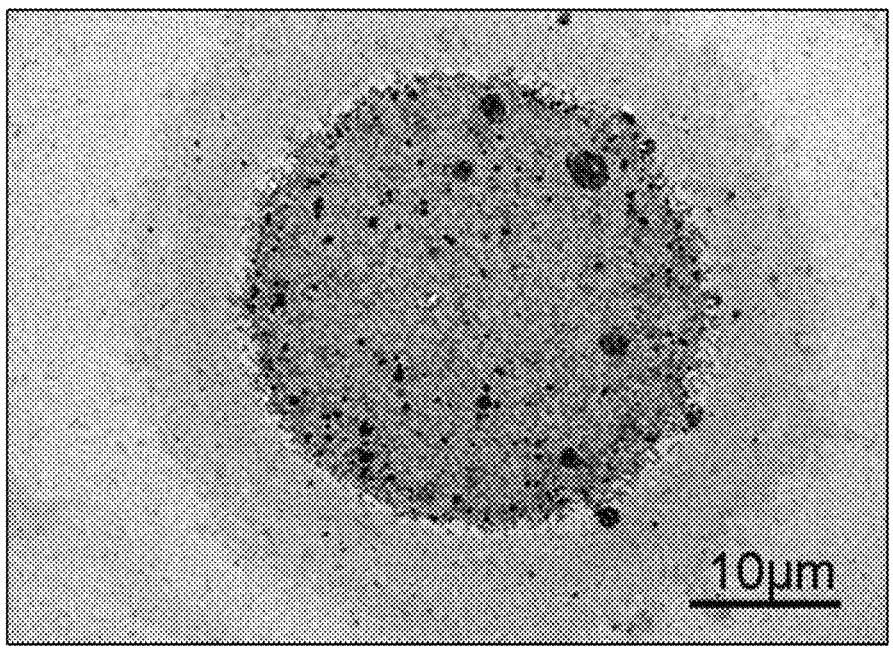
FIG. 1. Is an image derived from work done in 1975 that demonstrates the electro-dense halo of poly-lysine represented by transmission electron microscopy (TEM) following use of a coating on plates to facilitate attachment.

Vivex, the assignee of the present invention with its scientific research team of inventors has established itself as a preeminent manufacturer of advanced allograft biologic materials to support regenerative medicine initiatives. Vivex licensed a bone marrow cell line that was characterized with marrow-isolated adult multi-lineage inducible characteristics from the University of Miami. This patent publication, US 2015/0132266 A1, allowed for manufacturing and expansion, and has since been advanced to include a broader scope based on non-whole cell fragments including extracellular vesicles, as disclosed in U.S. Pat. No. 9,675,643 B2 and U.S. Pat. No. 9,687,511 B2, the contents of which are being incorporated by reference in their entirety herein.

Vivex additionally licensed U.S. Pat. No. 9,603,355 B2 for an amino acid polymer primarily defined as a polylysine. While other amino acids are included as substitutions in the composition, other properties of the materials defined in this patent have been observed. In addition to protecting the cells from freeze damage during storage, the formulation has been shown to be an effective tool for harvesting exosomes and enshrouding them as well. More recent work has shown that whole cells shrouded in the cryoprotectant exhibit unique and quite unexpected characteristics during preservation and later implantation.

The inventors developed several different processes for cell protection with this cryoprotectant, which have included a non-whole cell, and a bio-energized combination that used various fields of mechanical, electrical, and photonic stimulation to enhance the cell differentiation and activate the cells. One of the principal difference in those two products has been attributable to pH variation, and resulted in vastly different viable cell determinations on thawing. The lower pH in the first version of the cryoprotectant was 4.5-5.4 and generally formulated as less compatible with cell survival. What was impressive however, was the fact that the clinical performance has been outstanding and approaching 97% in the first 16,000 uses of the VIA® Graft product in patient care. The current composition of the present invention is developed to have a pH of 7.4 which is metabolically and physiologically more appropriate for cell survival.

Although previous prior art patents have assumed that the material protection primary purpose of cryoprotectants, such as DMSO based, has been to reduce, or eliminate crack propagation from ice crystal damage during freezing, the requirement for washing and decanting prior to use resulted in these protectants being washed away prior to implantation or culturing of the cells. The inventors of this invention have believed the explanation for clinical performance was stemming from coating the material with a protectant suitable for direct implantation. Other observations, recently made, have supported the hypothesis that the coating affects cell shape and that when coated, the cells do not flatten and attach when put in culture; instead they remain round. At first glance, the lack of attachment lead to the presumption that the cells are not viable, but confirmation with cell markers indicated they are alive, remain potent, and simply are not guided to attachment, this was a totally unexpected finding.

Cell attachment, long been accepted as a metric of affinity, depends on charge variation, surface roughness, material composition, and several studies have shown that modification of surfaces can be used to optimize biological activity. Limiting the discussion to the cryoprotectant, the scientific community has understood for some time that charge can be used to influence attachment, and guided by surface affinity between the cell membrane and surface features it is possible to tune the interaction between cells and surfaces to the extent that differentiation and proliferation can be tailored to specific lineage in cell phenotype, and in aggregate to attend tissue and organ morphology.

In the course of developing the use of the cryoprotectant of the present invention, solving initial challenges lead to better understanding novel properties that had not been defined in patents concerning cryoprotectants. The earlier work adjusted transition and thawing but did not identify assets to buffer inflammation, reduce premature differentiation, sustain regenerative potential, and facilitate donor-host interface during implantation of the grafting materials as was discovered in the present invention.

The key asset of coating the cells is derived from the cell attachment to the cryoprotectant. Using a polyampholyte to neutralize the hydrophilic amide linkage, a strong hydrophilic bond is established that protects the cell membrane, and provides a stable interface with environments external to the cells. This cell membrane boundary conditioned by the protectant at this material interface with the aqueous external milieu has been shown to interrupt crack propagation and in that way externally protects the continuity of the cell membrane. Additional value was sought to overcome the DMSO cryoprotectant issues of toxicity that lowers cell viability, and calls for a decant and rinse step before clinical use. These two properties guided the inventors' choice to adopt the technology and commercialize as a best in class Cellular Bone Allograft for bone regeneration applications.

During the testing and developing of quality guidelines, the lack of cell attachment in culture, the unusual round cell morphology, and the challenges of assaying viability presented new challenges to the inventors. However, in the process of defining those parameters and establishing quality assurance and product release standards, the inventors gained new insight into the cryoprotectant that the charge of a carboxylated poly-lysine polyampholyte protectant provides the cells an attachment paradigm that without apical-basal polarization retards flattening and keeps the cells round. With molecular surfaces, or faux attachment facilitated by binding ligands surrounding the cell, a second advantage to the cells emerges that supports the fact that during early inflammation phases of the wound repair, donor, or implanted cells are not exposed to granulation tissue cytokines. Without this early exposure, and in absence of attachment, cytokines that nurture regeneration rather than fibroblast proliferation are the more effective modulator of the live cell fraction. A two-dimensional image derived from work done in 1975 demonstrates the electro-dense halo of poly-lysine represented by transmission electron microscopy (TEM) following use of a coating on plates to facilitate attachment (FIG. 1). The relevance of this image in comparison to a recent Scanning Electron Microscope (SEM) is remarkable.

Figure 2:
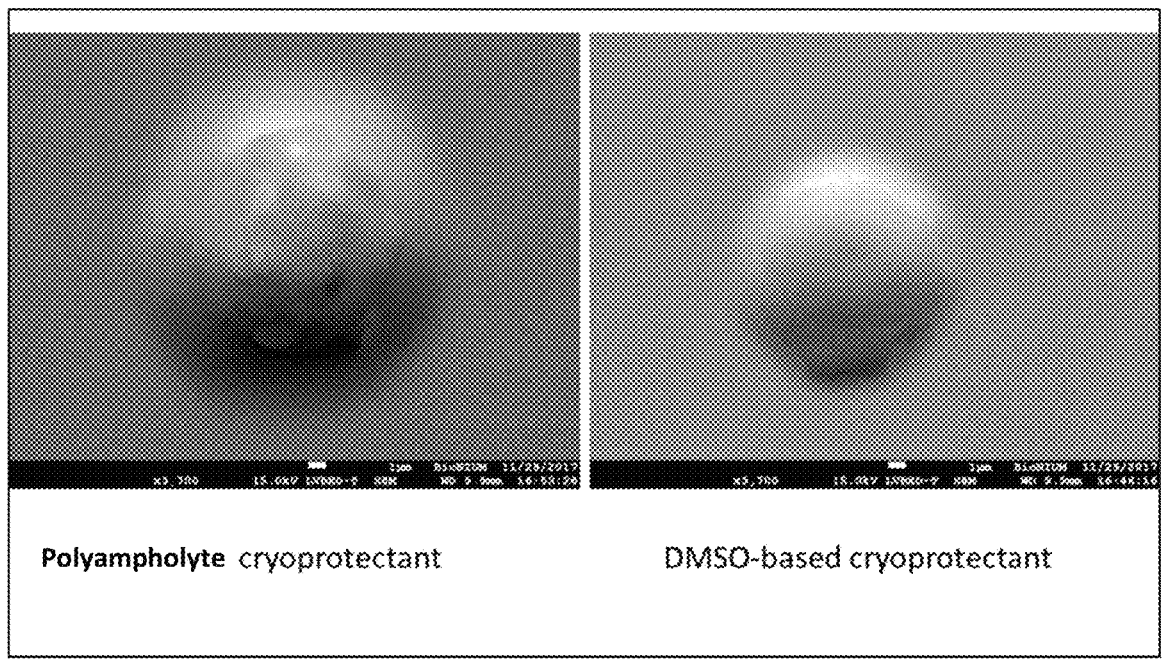
FIG. 2 is a comparison of a polyampholyte protected cell on the left and a DMSO treated cell on the right.

What makes the observation impressive emerges in the context of the recent scanning electron micrograph where the 3D structure that is presented, starkly contrasts the difference between the polyampholyte cryoprotectant treated cells and DMSO treated cell lines. The abundance of charged field is appropriate to a polyampholyte which provides a charge (FIG. 2). These cationic coatings, including poly-lysines were developed for positive charge—essentially to facilitate the electronegative charge on cells to be more avidly bound.

Figure 3:
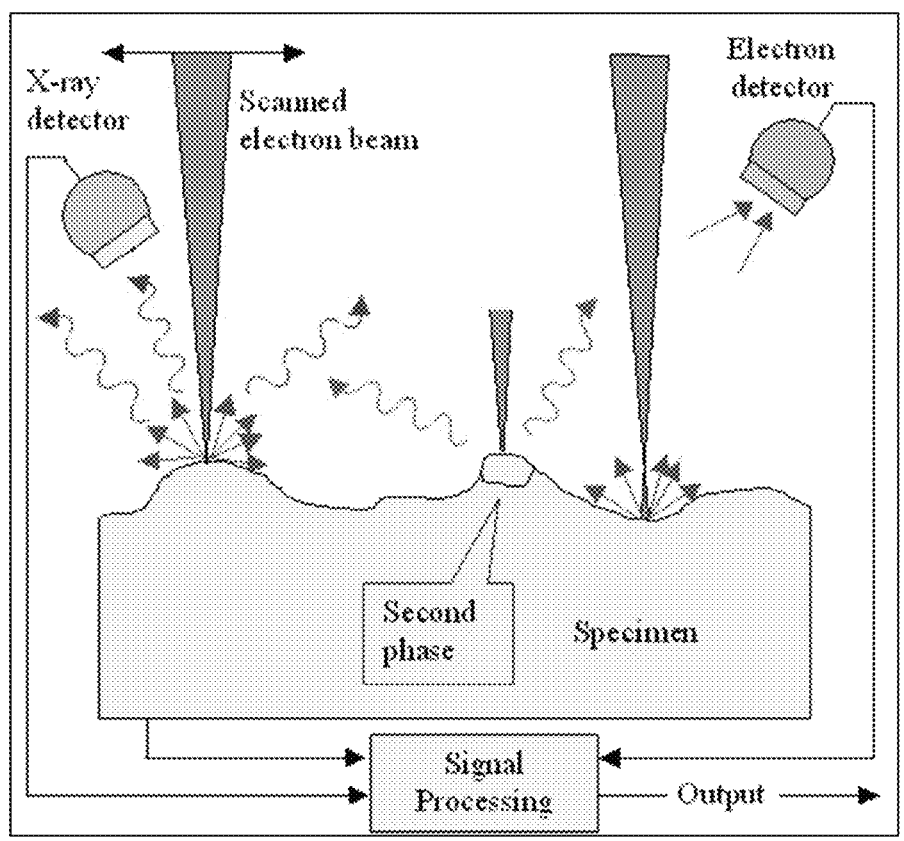
FIG. 3 is a schematic depiction of how a SEM, scanning electron microscope 3D image is produced.

Scanning electron microscopy is an accepted tool for evaluating structure, composition, and even isotope variations of materials. While the theoretical design straightforward, shown schematically in FIG. 3, there are many intricacies to the analysis that can be accounted.

The evaluation of the viable cell product compositions developed by the inventors, provided additional insights that refine expectations for protection, and extend additional benefits.

Various protective roles of the cryoprotectant include protection from freeze-thaw damage; crack propagation inhibition; insulation from early inflammation following transplantation; retention of non-differentiated cell phenotype; attachment protection—delayed flattening of cells following implantation; donor—host contact facilitation; paracrine exchange; metabolic neutrality; and cationic pharmacology enhances cell attachment.

Several observations have been developed by the present inventors to account for these additional benefits: The cryoprotectant completely envelops the cells. Polyampholyte materials retain intense, but balanced charge when used to protect the cells. This charge is evident in SEM images. Cells retain viability and sense attachment even though still round. The protectant of the present invention protects the cells whereas DMSO is not retained on the cells for protection. The protectant remains surrounding the cells for up to 6 days, is normally metabolized, and protects transplanted cells from macrophage digestion during the granulation phase of inflammation and wound healing in contrast to the DMSO protected cells that are rinsed removing the protectant and thus exposing the cells to this condition at the onset of implantation.

To better clarify the discovery process and further a basis for claims of the present invention, it is important to understand the methods and directions that have guided new understanding and directed additional invention.

Figure 4:
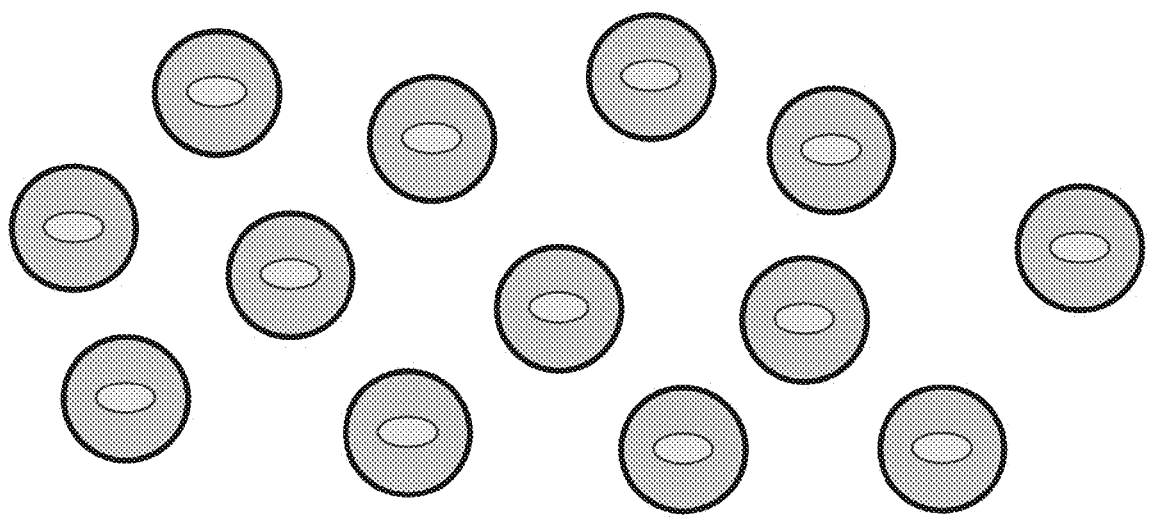
FIG. 4 is a depiction of cells isolated during the process.
Figure 5:
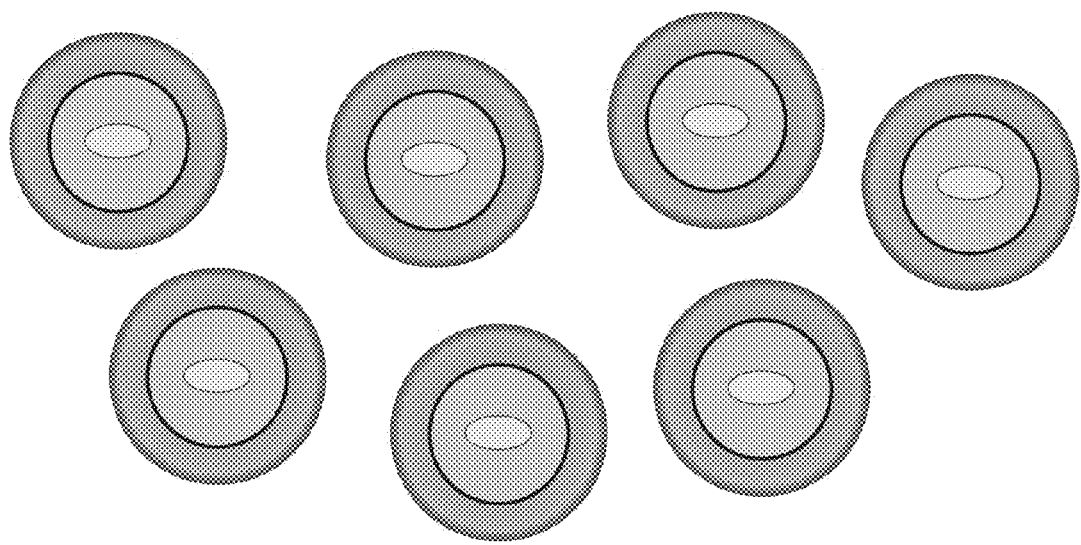
FIG. 5 is a depiction of cells coated in cryoprotectant.
Figure 6:
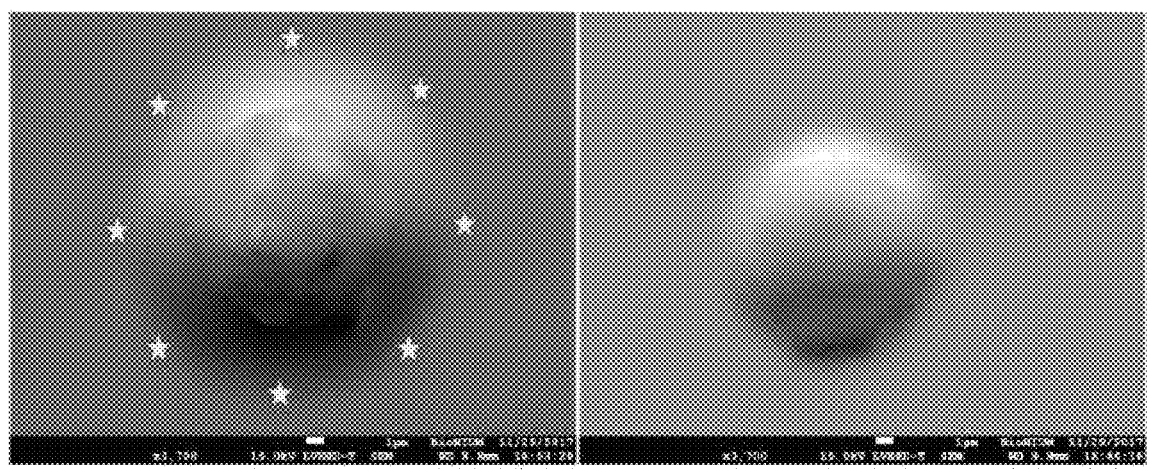
FIG. 6 is a SEM image showing the electron dense halo (shroud) on the polyampholyte protected cell on the right and a DMSO treated cell on the right.
Figure 6:
Figure 7:
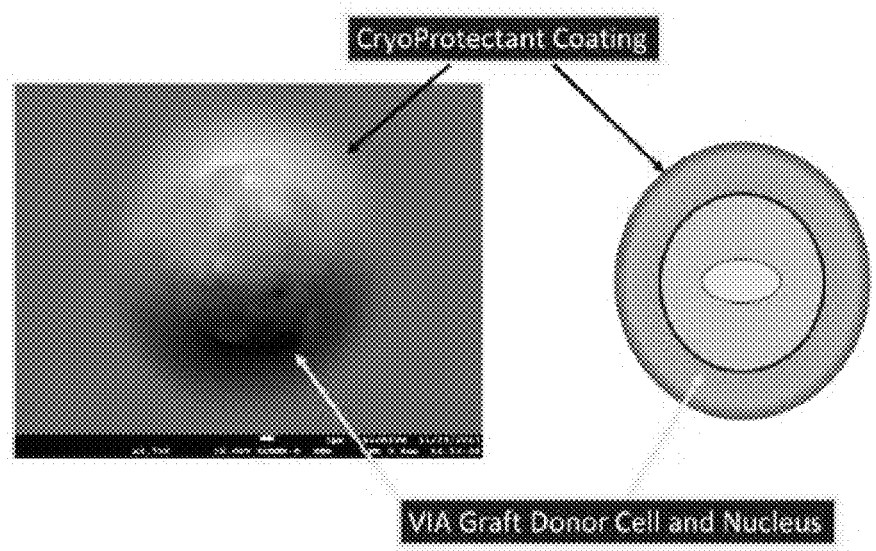
FIG. 7 shows a depiction of the halo.

In one exemplary embodiment, the first steps in developing the cellular bone matrix is to separate bone marrow cells. This is well defined and has been extended to include not only whole cells, but also cell fragments, vesicles, ligands, lipid rafts, exosomes, organelles etc. Each permutation has been paired with a broad term for the cryoprotectant, polyampholyte. FIGS. 4 and 5 illustrate the cells isolated during the process and the cells coated in the cryoprotectant. Note the halo surrounding the cells. In addition to providing protection from crack propagation as intended from its use in cell preservation, this electro positive surrounding field of charge also offers several benefits to the cell during placement, to the host during chemotaxis, and to the regenerative construct during cell-cell communication and paracrine intercellular exchange.

The first observation of the development was that the cells did not plate, and while viability was apparent, the floating, equibuoyancy of the cells in the medium did not match any available cell culture literature. The cells were alive as determined by fluorescent nuclear markers, but did not allow trypan blue or other cellular viability markers to be used with any assurance. However, after several days in culture and with support of cell media, cells did begin to flatten, attach and assume the morphology of cells better typified as mesenchymal stem cells (MSC). These cells also could be identified using flow cytometry to bear common ligands that are consistently shown to be a part of MSC known markers.

The gulf guiding the proof is part of the new understanding that in part forms the basis for this invention. A highly charged coating used to protect the cells also creates a cell surface, cell matrix bond that makes the cells think they are attached. Rather than flattening to one surface, the cells remain completely surrounded by a high affinity binding that protects from freezing, but more importantly buffers the cells from the surrounding materials during placement or implantation.

Figure 8:
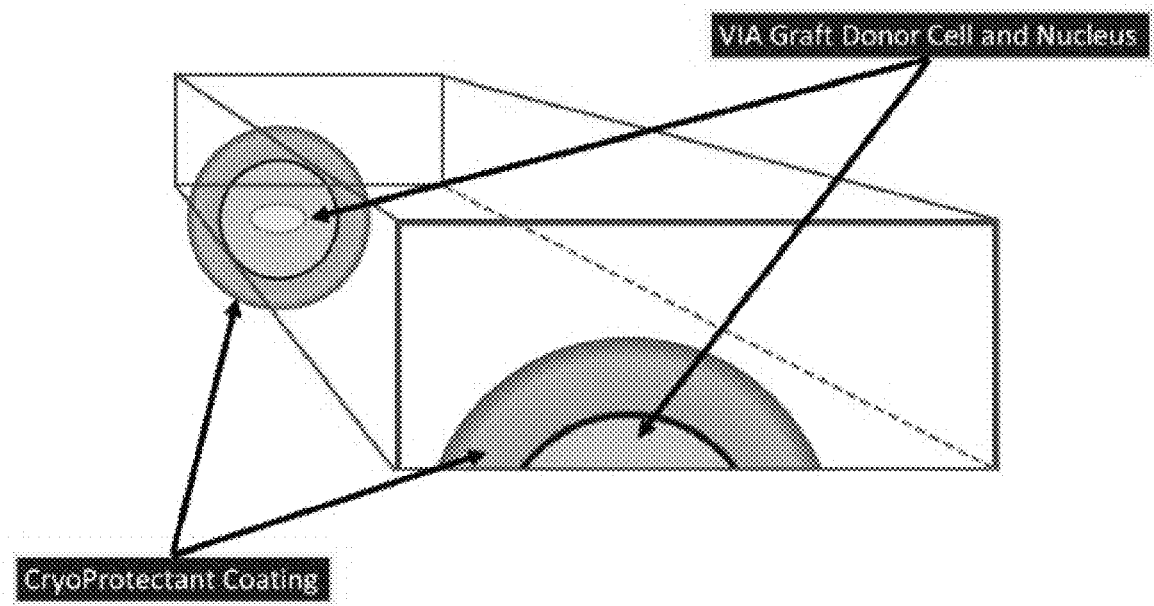
FIG. 8 is a depiction of the cryoprotectant coated cells.

There are actually two phases of inflammation that take place during wound healing, and despite the careful controlled situations of surgery the intervention is still a wound that requires repair and integration. The first phase is the initiation phase that causes the heat, pain, swelling, and redness associated with inflammation. Subsequently, there is a second phase called the resolution phase that reverses the initiation phase and allows tissue regeneration. As long as these two phases of inflammation are balanced, healing occurs. One of the clear and distinct advantages of the bonding shroud of cryoprotectant is its ability to surround and protect during the early phase of inflammation. Rather than driving the viable cell phenotype of the donor in response to the catabolic cytokines, the shielding instead allows the cells to be exposed to the subsequent regenerative formation, shown in FIG. 8.

Figure 9:
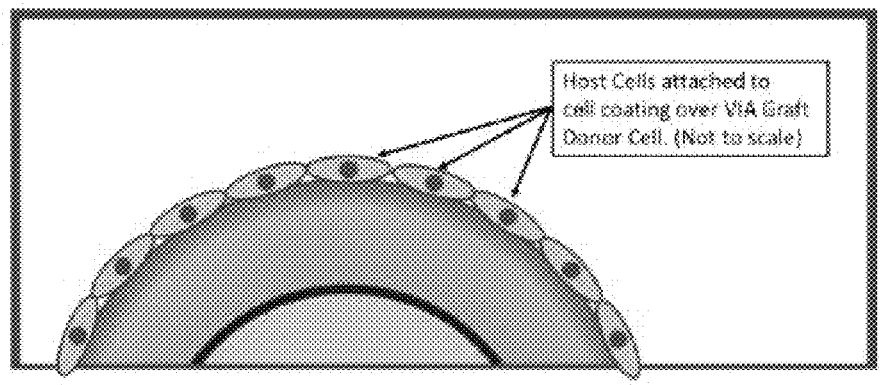
FIG. 9 is a schematic flow chart showing the host donor cell relationship with host cells attached to the cell coating shroud, the donor cells and host cells, as illustrated, are not to scale.
Figure 10:
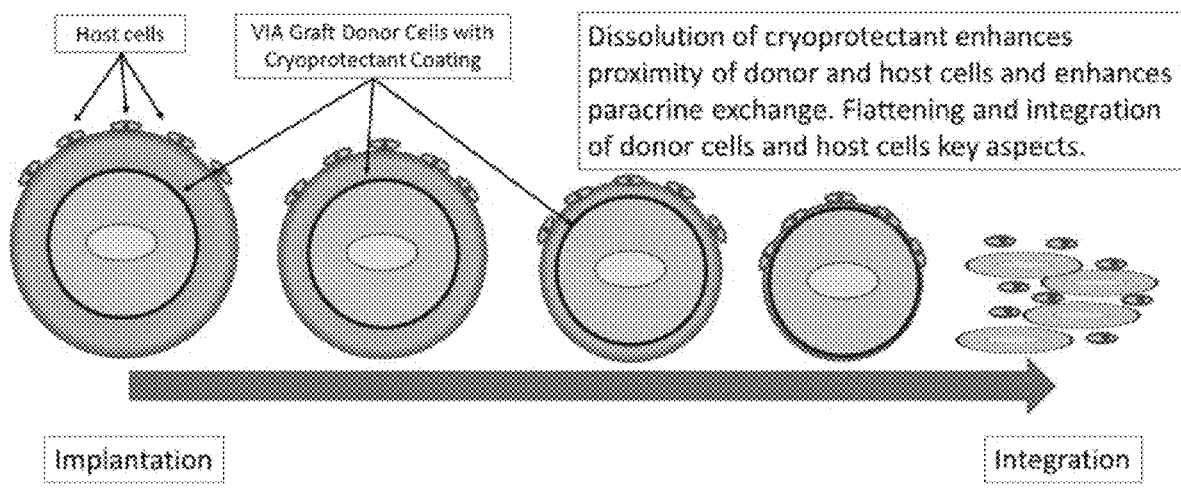
FIG. 10 shows the metabolic absorption of cryoprotectant.

Secondary to the protection afforded the donor cells, the host tissue also is able to attach to the coating and this brings the donor and the host cells in close proximity during the regenerative phase. This close proximity is effective in facilitating the paracrine interface that further stimulates and integrates the regenerative response as shown in FIGS. 9 and 10. The host cells are intentionally shown smaller in size compared to the donor to illustrate the attaching to a donor cell, in reality, the host cells are typically the same size of the donor cell as evidenced in FIG. 11.

Figure 11:
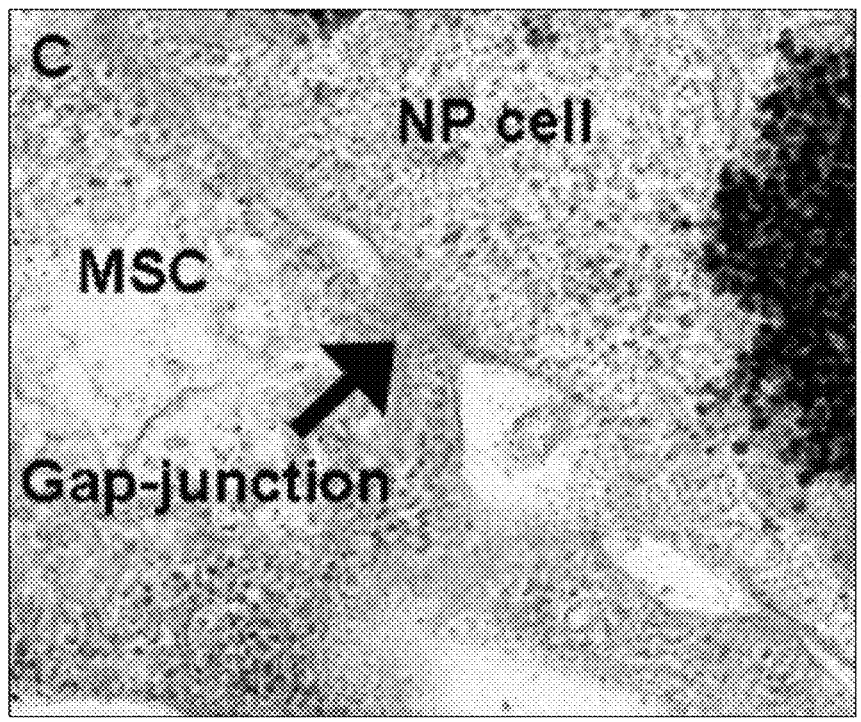
FIG. 11 shows the cell exchange of exosome from "Bi-Directional Exchange of Membrane Components Occurs during Co-Culture of Mesenchymal Stem Cells and Nucleus Pulposus Cells" by Sandra Strassburg, Nigel W. Hodson, Patrick I. Hill, Stephen M. Richardson, Judith A. Hoyland.

Metabolism of the coating results in approximation of host cells attached with donor cells that are coated. As the cells come together, current understanding supports the fact that genetic material is exchanged. By providing a cryoprotectant surrounding the donor cells, and also defining a composition that accentuates attachment of host cells, a novel new use is identified that refines and optimizes direct cell connections for epigenetic exchange. This is shown in FIG. 11.

Figure 12:
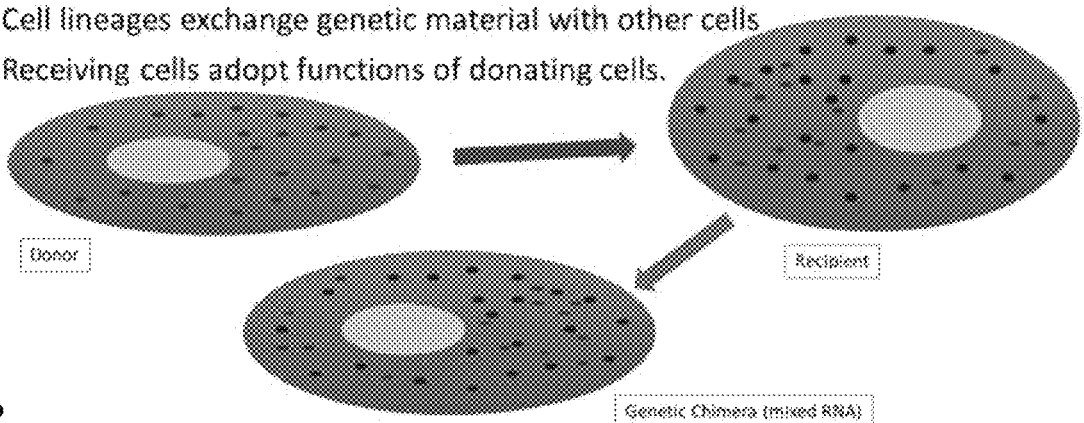
FIG. 12 shows the principle of genetic transfer with colored representing the difference and gain of function.

The theory behind exosome expansion and epigenetic regulation has evolved to the point that molecular tracking occurs and can be shown between cells. Depicted in FIG. 12, the colored dots represent difference and the gain of function the bi-colored inclusions. The donor cell exchanges material such as exosomes with a host or patient's cell. On cell division, a genetic chimera (mixed RNA) cell has the genetic encoded material of both cells. This is extremely beneficial to cell replication during the healing process.

Figure 13:
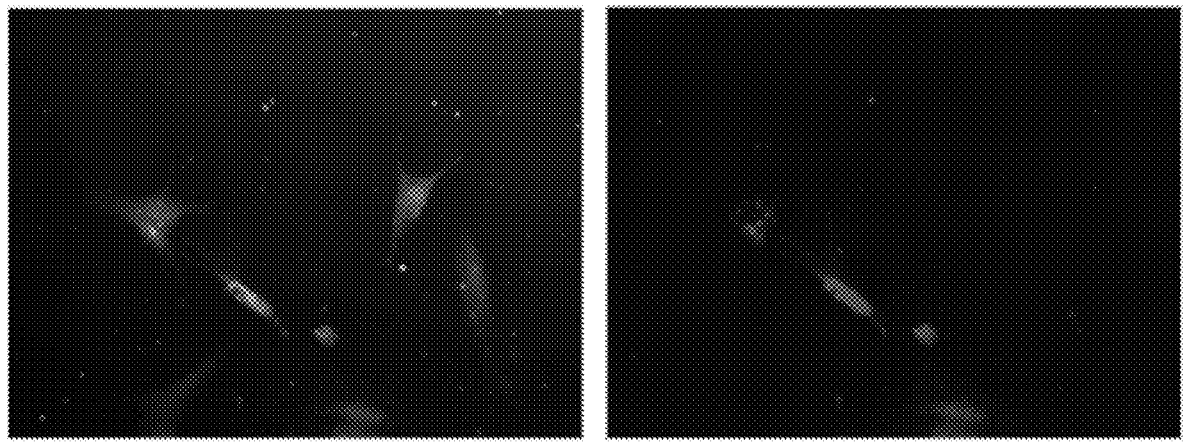
FIG. 13 shows how co-culture exchange is demonstrated with CFDA staining on the left in green and DiI staining on the right in red.
Figure 14:
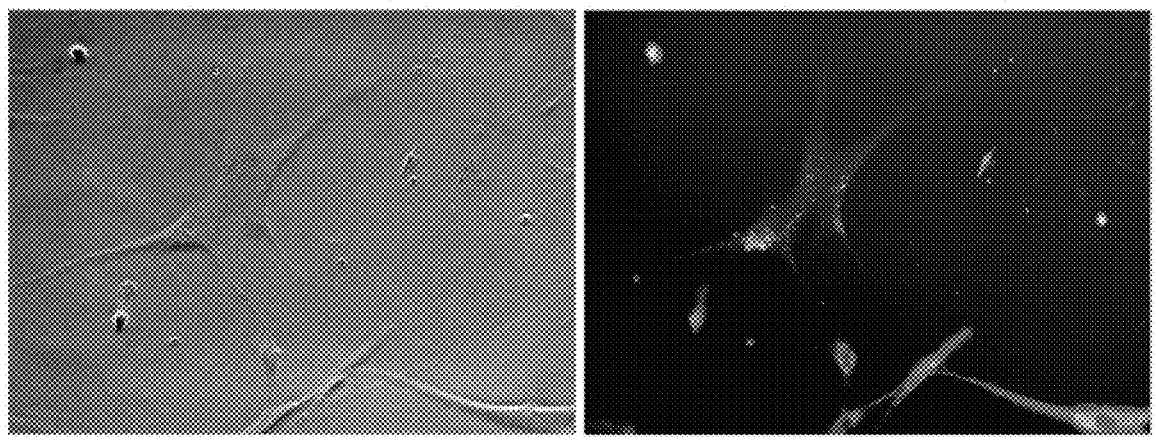
FIG. 14 shows evidence of genetic exchange of intracellular material after 3 days of co-culture.

FIG. 13 provides laboratory evidence of co-culture exchange with mesenchymal cell population expanded and divided into two equal portions. One portion stained with for exosome membrane DIL and Second portion stained with cytoplasmic stained CFDA (Carboxyflourescein diacetate). While FIG. 14 shows 3 days of co-culture evidence of genetic exchange demonstrated exchange of intracellular material, these figures together confirm the findings and are significant to the current understanding of the present invention.

Figure 19:
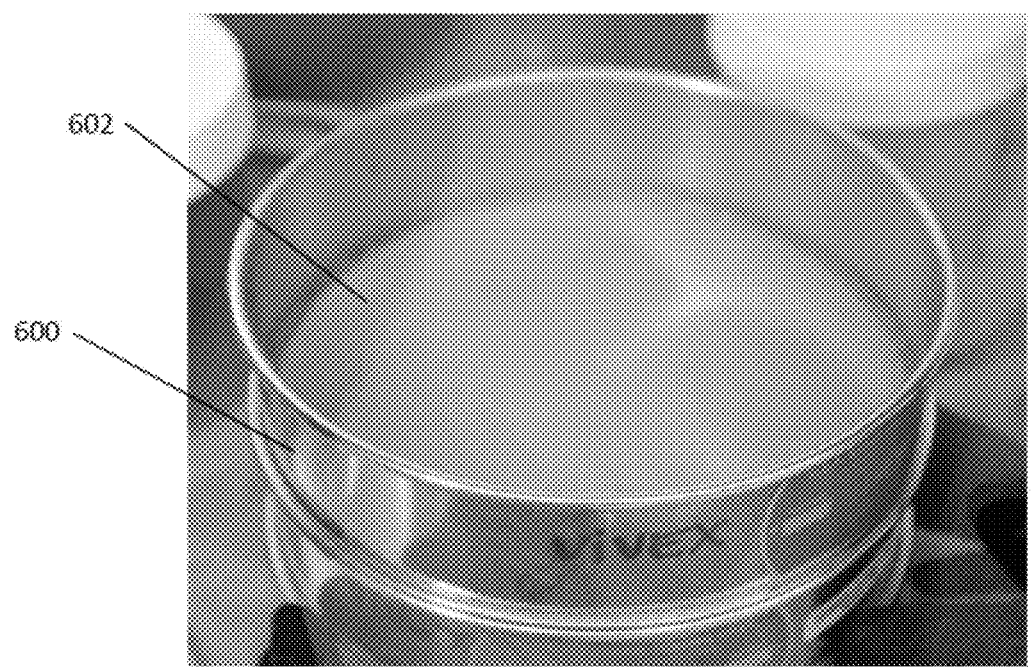
FIG. 19 is a photograph of an exemplary sieve device having sieves sized to separate the solid material.

The step of mechanically separating these cellular components of bone marrow 200 from the cadaverous bone is next performed. Transferring the bulk cortical-cancellous bone chips into a new jar with a CBT-Mixer in the jar. The bulk cortical-cancellous bone chips 206 will go through four cycles as summarized in the table below. Each cycle, after cycle 1, contains three steps using a bone tumbler 500 and sieve set 600. The sieve set 600 has screens 602 of various sizes, for example 500 μm and 180 μm, as shown in FIG. 19.

| Step | Cycle 1 | Cycle 2 | Cycle 3 | Cycle 4 |
|---|---|---|---|---|
| Bone Tumbler | 30 minutes. Using 500 mL Processing Media | 30 minutes Using 500 mL Processing Media | 30 minutes Using 500 mL Processing Media | 30 minutes Using 400 mL Processing Media |
| Sieve Set | Use the 500-μm and the bottom pan sieve. Discard decanted fluid. | Use the 500-μm, 180-μm and bottom pan sieve. Collect decanted fluid. | Use the 500-μm, 180-μm and bottom pan sieve. Collect decanted fluid. | Use the 500-μm, 180-μm and bottom pan sieve. Collect decanted fluid. |
| Centrifuge | N/A | Use decanted fluid. | Use decanted fluid. | Use decanted fluid. |

For completeness of the understanding of the invention as described above, an example of one method of recovering the biological material from bone marrow is disclosed. It is understood that other sources and methods can be used to collect biologic material such as from bone, blood, fat cells, including the isolating of whole cells from these alternative sources from living hosts or cadavers and these cells would equally benefit from the present invention.

With reference to the exemplary method which is a tissue regenerative biological composition 100 made from bone marrow 200, it is believed best understood by the methods used to process and recover the biological composition, as illustrated in the FIGS. 15-20.

Figure 15:
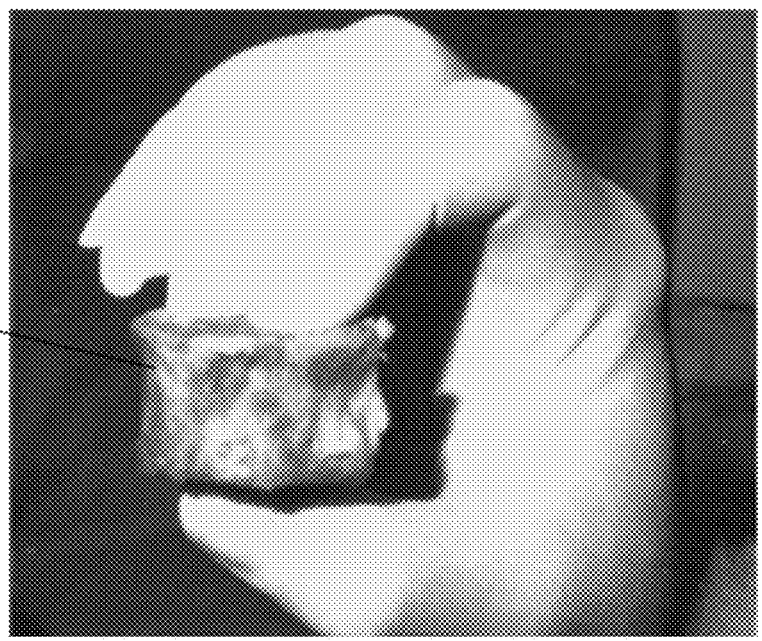
FIG. 15 shows a photograph of a cut vertebral body taken from a spine of a cadaver donor.
Figure 16:
FIG. 16 shows a photograph of the vertebral body after being cut into cubic pieces and immersed in a packing media.
Figure 17:
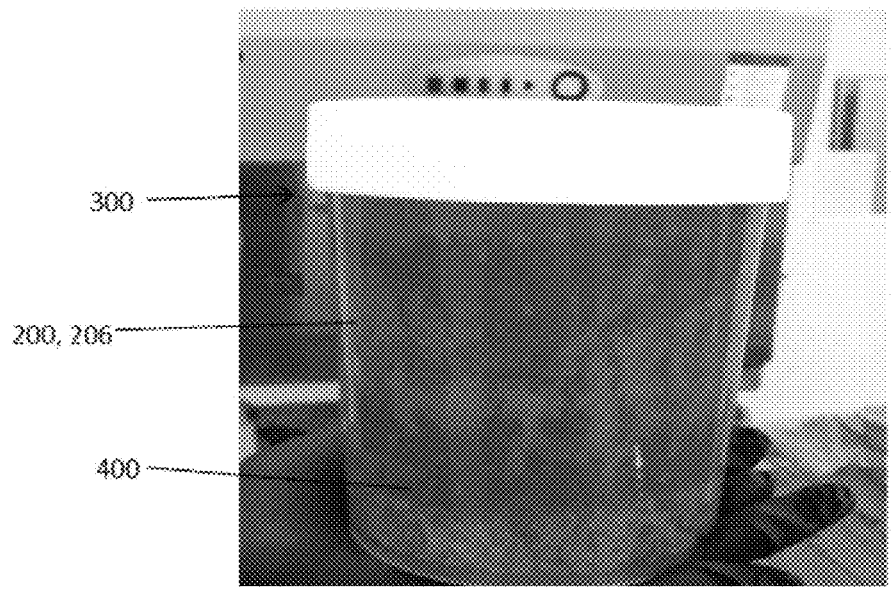
FIG. 17 shows a photograph of the bulk bone material after being ground and immersed in packing media and placed in a jar for later tumbling.
Figure 18:
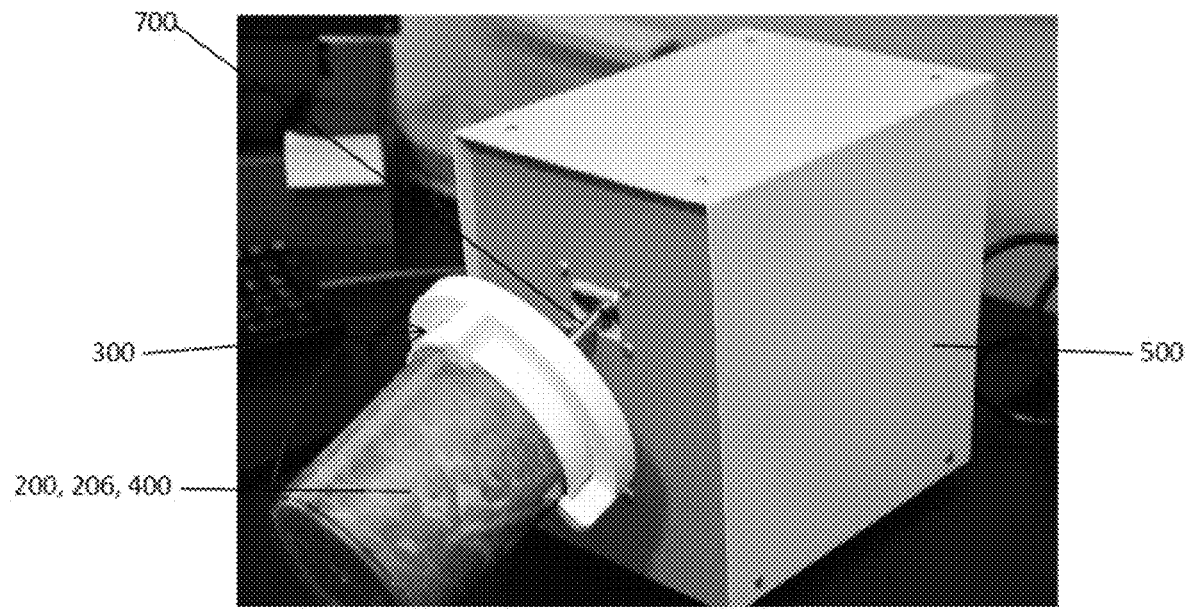
FIG. 18 shows a photograph of the jar with a CBT-Mixer connected to a tumbler.

The first steps are to collect, recover and process bone marrow 200 from a cadaver donor. To do this, the spine is removed aseptically from the cadaver and the resultant spine segment is covered by cold media. The cold media has 0.5 ml of Heparin; 10,000 units/ml per 500 ml of DMEM. DMEM is a sterile solution with low glucose (lg/L), Sodium Pyruvate; without L-glutamine, or HEPES. This cold media is used for packaging the spine segments for later processing. At this point the spine segment includes a plurality of vertebral bodies 202. The clinical technician must remove as much soft tissue as possible and cut each vertebral body 202 with a saw. These vertebral bodies 202, once cleaned, of all adherent soft tissue around the cortical surfaces will look as shown in FIG. 15.

Once a cleaned vertebral body 202 is obtained, the next step involves cutting each vertebral body 202 into pieces, each piece 204 roughly 1 cm³. The cut pieces 204 being immersed in a packing media 400. The exemplary packing media can be DMEM with 0.5 ml Heparin and 1.25 ml of DNAse added.

Once all the vertebral bodies 202 have been cut, the pieces 204 are taken to the bone grinder. The bone is ground into 4-10 mm pieces using packing media 400 to help the pieces go through the grinder. The ground bone 206 (bulk cortical-cancellous crushed) and all of the packing media 400, estimated volume of 500 ml are transferred into a jar 300 where 0.5-1.0 ml of Gentamicin is added to the jar 300 with ground bone 206 and packing media 400. At this point, the crushed bone 206, including cellular soft marrow 200, is intermixed.

Figure 21:
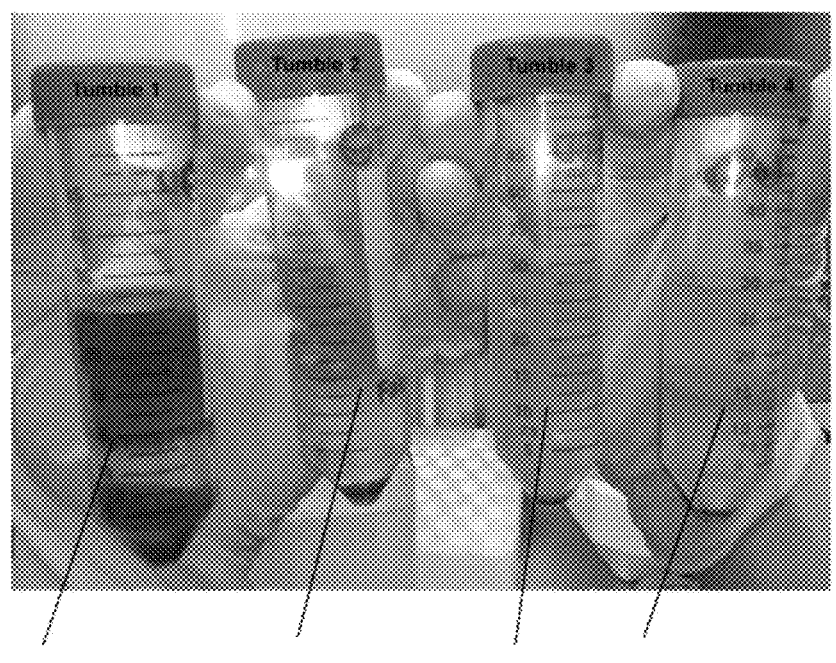
FIG. 21 is a photograph showing the four tumbling steps 1-4 by exemplary collection and Ficoll separation of the decanted fluids, the fluid in tumble 1 being completely discarded to remove unwanted debris.

In cycle 1, the decanted fluid 210 is discarded. To best understand this, an exemplary FIG. 21 shows conical tubes with the decanted fluids after each cycle followed by Ficoll separation. Tumble 1 or Cycle 1 has most of the unwanted cells and debris as evidenced by its dark and red appearance whereas each subsequent cycle 2, 3 and 4 are progressively cleared. This FIG. 21 is only to illustrate the effects of multiple tumbles 1-4 and the value in discarding the decanted liquid 210 after the first tumble 1.

After each subsequent sieving of the bulk bone material 206, the decanted fluid 212, 214, 216 containing the mixture with whole cells is collected and put into a collection jar. When the next three cycles are complete and the decanted fluid is all placed in the collection jar comingling the fluids 212, 214 and 216 to form a decanted fluid 220. Then the centrifugation of the combined decanted fluid 220 occurs by placing the fluid 220 in a number of 250 ml conical tubes using a 100 ml pipette. The centrifuge is programmed to 280×g for 10 minutes at room temperature, preferably about 20 degrees C. The fluid 220 is passed through a blood filter to further remove any bone or spicules or clumps from the suspended cells. This completes the step of centrifuging and filtering. At this point, the mixture including whole cells 240 has been separated from the soft marrow tissue 200 and the remaining cancellous and cortical bone is discarded.

Figure 20:
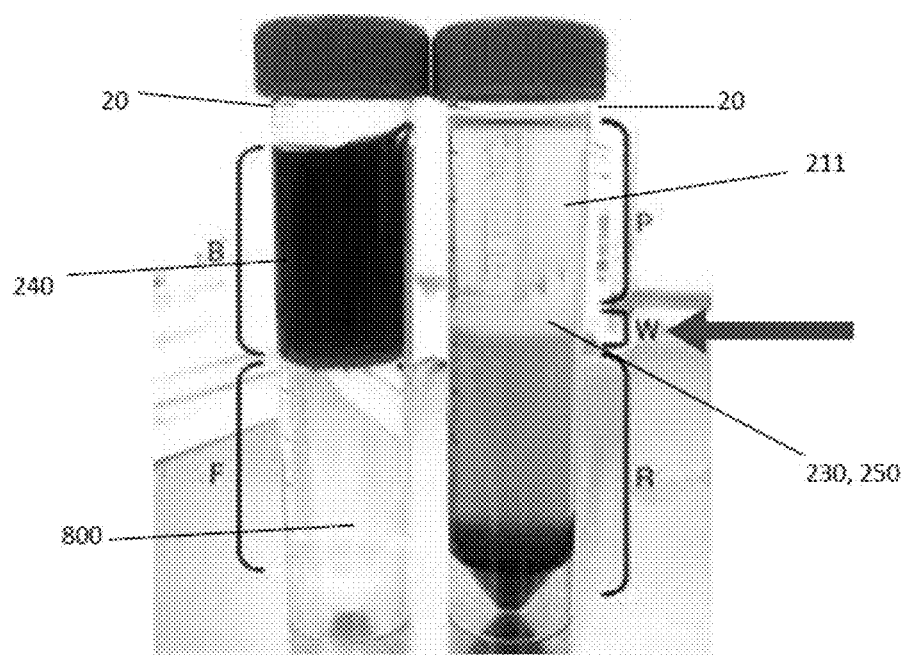
FIG. 20 shows a photograph of two 50-ml vials, the one on the left being prior to centrifuging with the Ficoll that is commercially available at the bottom and the material above it. The 50-ml vial on the right is after centrifuging showing the non-whole cell fraction interface layer.
Figure 22:
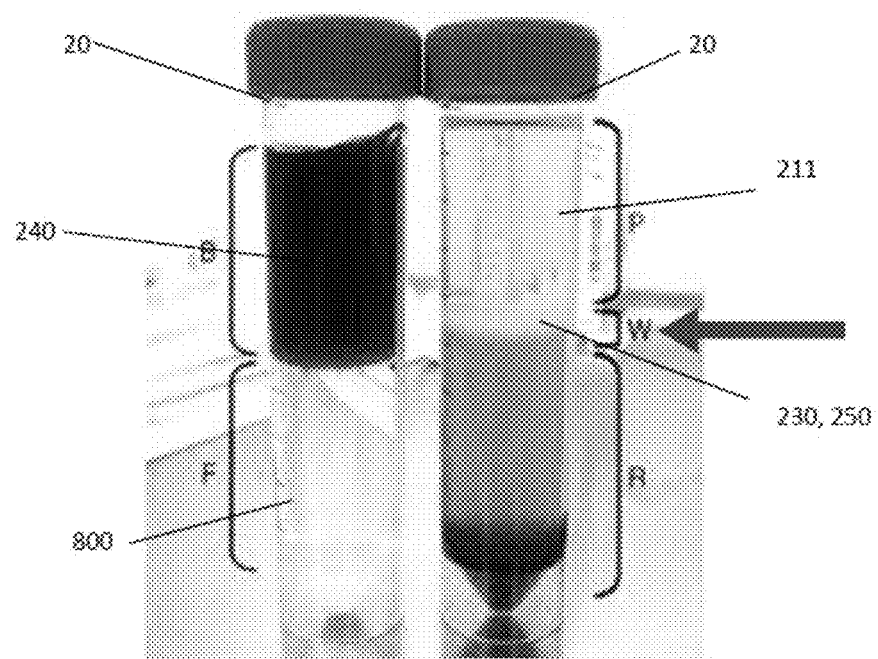
FIG. 22 shows a photograph of two 50 ml vials, the one on the left being prior to centrifuging with a sucrose gradient that is commercially available at the bottom and the material above it. The 50-ml vial on the right is after centrifuging showing the non-whole cell fraction above the interface layer.

After this, as shown in FIGS. 20 and 22, the step of separating the cells 240 from the non-whole cellular components can occur by a density centrifugation, if so desired. The whole cells 240 are in the interface and the non-whole cell components are in the supernatant above the interface. The mixture is placed in 50 ml conical tubes 20 with Ficoll 800 and undergoes a Ficoll-Paque separation under centrifugation wherein a cell density gradient is established by spinning at 400×g for 30 minutes at room temperature, preferably about 20 degrees C. The mixture includes cellular or non-cellular components or a combination thereof. All fluid 211 above the interface 230 can be removed which includes the desired non-whole cell components and which excludes the whole cells 240, 250 or all the fluid 211 and the interface 230 can be removed together.

Typically, non-whole cell fragments, or membrane components have a diameter of 40-100 nm and can be separated within a density of 1.13-1.19 g/mL in a sucrose solution, and can be sedimented by centrifugation at 100,000 g. In fact, these fragments, or cell fractions, or microvesicles, have been collectively referred to as exosomes. Ranging in size from 20-1000 nm in diameter, they have been similarly referred to as nanoparticles, microparticles, shedding microvesicles, apoptotic blebs, and human endogenous retroviral particles. There are few firm criteria distinguishing one type of microvesicle from the other.

Following removal of the cell fraction, the supernatant is further filtered through 0.45 and 0.2 µm filters. Exosomes are further collected and separated within the suspension in multiple centrifugation steps with increasing centrifugal strength to sequentially pellet cells (300 g), microvesicles (10,000 g) and ultimately exosomes (100,000 g). Cells can be deliberately removed to achieve a mixture having the non-whole cell fragments and microvesicles or can be kept forming a combination of whole cells and non-cellular components.

Subsequent separation using density gradient-based isolation, using sucrose or commercially available prep can be applied to obtain more pure exosome preparations. Recent reports encouraging the use of iodixanol-based gradients for improved separation of exosomes from viruses and small apoptotic bodies are considerations left open to be adopted or adapted in refinement. Differing from sucrose, iodixanol forms iso-osmotic solutions at all densities, thus better preserving the size of the vesicles in the gradient, and both technologies are available to best isolation technology. In addition to these traditional isolation techniques, easy-to-use precipitation solutions, such as ExoQuick™ and Total Exosome Isolation™ (TEI), that have been commercialized reduce the need for expensive equipment or technical know-how. Although their mode-of-action has not been disclosed or validated, these kits are commonly used.

Figure 23:
FIG. 23 is a representative photograph of the final packaging.

Once the mixture is completed, the method can include additional steps. This leads to the use of a bone blend 102 shown in FIGS. 23 and 24, preferably from the same vertebral bone or at least bone from the same donor.

When the mixture is prepared, it can have whole cells exclusively, or in combination, or even no whole cells, but will have the mechanically selected non-whole cellular components including vesicular components and active and inactive components of biological activity, cell fragments, cellular excretions, cellular derivatives, and extracellular components.

In one embodiment, the composition includes the whole cells in the mixture. In that embodiment, it is possible to provide bone particles with the mixture either in the mixture or separately to be combined at the time of use.

Figure 24:
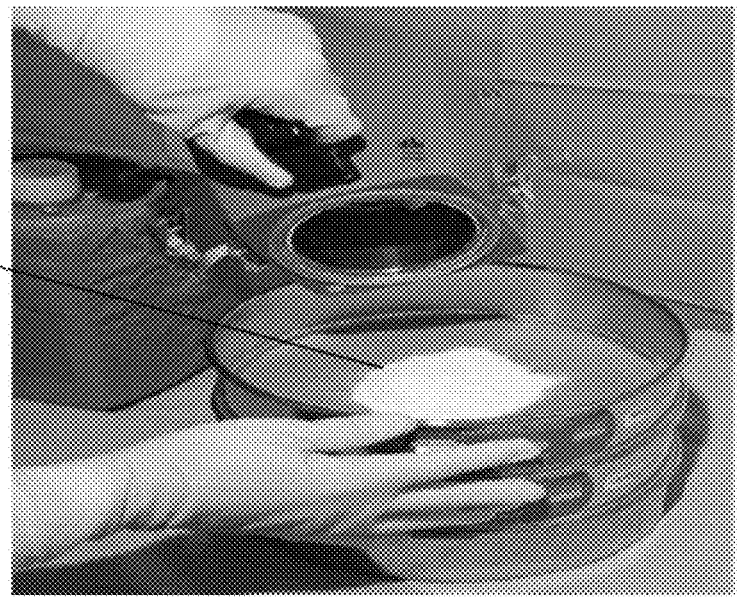
FIG. 24 is a photograph showing the ground bone.

In one embodiment, the bone is ground to a particle size of 100-300 µm, see FIG. 24. The bone mixture has 1.5 cc of mineralized cancellous bone 104, 1.5 cc of mineralized cortical bone 105 and 2.0 cc of demineralized cortical bone 106 yielding 30 percent, 30 percent and 40 percent respectively of the total 5 cc (5 gram) of bone material 102. The ranges coincide with the 1 cc of mixture when resuspended in 3 cc of saline to provide a bone particle and mixture for implantation, which can be by packing, injection, scaffolding or any other suitable means, into a patient in a fracture healing procedure, by way of example.

Other ranges of bone particle sized and mixture can be employed depending on the application which, in this example, was bone regeneration. Lower volumes and concentrations may be more suited for less intrusive bone repairs or more if larger if larger amounts of material are needed as in a hip defect or repair.

A cryopreservation liquid according to the invention is obtained by dissolving a polymer such as poly-lysine in physiological solutions by 1-50 w/w %; preferably by 2-20 w/w %, particularly preferably by 3-15 w/w %, and more preferably by 5-10 w/w %. The physiological solutions to be used are a physiological saline as well as culture media for culturing various cells and tissues. For example, Dulbecco-modified eagle MEM culture medium (DMEM) may be one of the preferable culture media. In place of, or in addition to poly-lysine, polyallylamines may be used. In place of these, or in addition to at least one of these, a compound(s) to be used is/are selected from other polyamines such as amino-group-introduced polysaccharides, and poly-amino acids such as poly-arginine, poly-glutamic acid and poly-aspartic acid; also a polysaccharide compound(s) that is/are selected from dextran, dextrin, pullulan and chitosan as well as polycarboxylic acid such as polyacrylic acid.

Among these polymers, preferable are polymers having a structure obtainable by polymerization of a monomer compound(s) that have both cationic and anionic substituent groups within the same monomer molecules; and especially preferable is poly-amino acids. In other words, especially preferable is a polymer having a repeating unit that has both amino and carboxyl groups. Poly-lysine to be used can be either ε-poly-L-lysine or ε-poly-D-lysine or α-poly-L-lysine. Cryoprotectant polymers have molecular weights between 100 and 100,000. The most preferable polymers fall into a group of ε-poly-L-lysine routinely used as food additives. These are either synthesized by enzymes or produced by the *Streptomyces* fungi and have the average molecular weights of 1000-20,000, and particularly those of 1000-10,000 with polymerization degrees ranging between 15-35, and those with 20 or lower are attempted to be produced. The average molecular weights or the average polymerization degrees are easily measurable by sodium dodecyl sulfate-polyacrylamide gel electrophoresis (SDS-PAGE), by using an electrophoresis apparatus and densitograph. Standard protein markers are used for the measurement. The poly-lysine may be heat-treated to increase its molecular weights greater than 30,000 and used as the polymer compound. However, the molecular weight range mentioned above is preferable due to the increasing viscosity with molecular weight. Because the poly-lysine having a free terminal carboxyl group has side-chain primary amino groups, their partial amidation by dicarboxylic anhydrides greatly gives excellent miscibility and solubilization performance described later. Other particularly favorable polymer compounds also adoptable according to the invention are polyallylamines with average molecular weights of 1000-1,000,000, preferably 1000-20,000. For examples, such adoptable polymers are: aqueous solution of the allylamine polymer (PAA-03 of Nitto Boseki Co., Ltd.) added with acetic anhydride or acetic acid; and the partially-methoxy-carbonylated allylamine polymer (PAA-U5000 of Nitto Bosch Co., Ltd.). The allylamine polymer, in same manner with the poly-lysine, has as side-chain groups primary amino groups only, but density of the primary amino group per unit molecular weight is larger in the allylamine polymer than in the poly-lysine. And, when the allylamine is partially carboxylated, obtained polymer compound is considered to act in same manner with partially-carboxylated poly-lysine mentioned later.

Preferably, the amino groups of the polyamine are partially blocked by being carboxylated or acetylated with carboxylic acid anhydride(s). This blockage is done by the carboxylation or acetylation of the amino groups to the degrees of preferably 50-99 mol %, particularly 50-93 mol %, more preferably 50-90 mol %, still more preferably 55-80 mol %, and the most preferably 58-76 mol %. About 50% of the amino group would be blocked by being reacted with 52-53 mol % of anhydrous carboxylic acid on basis of molar amount of the amino groups in the polyamine. In a normal reaction condition, 90-95% of the amino groups would be blocked when reacted with 100 mol % anhydrous carboxylic acid. The blocking rates above or below the above-mentioned ranges would decrease cryopreservation effects. Carboxylic acid anhydrides adoptable herein include acetic anhydride, citric anhydride, succinic anhydride, glutaric anhydride, malic anhydride, fumaric anhydride and maleic anhydride. Among these, succinic anhydride and acetic anhydride are particularly preferred.

However, polyamine with amino groups not blocked as free may also be used; thus adoptable are the degrees of carboxylation and acetylation throughout a range of 0-100 mol/mol %. In the present invention, polycarboxylic acid in which a part of the carboxyl groups is aminated may be used. More specifically, polycarboxylic acid may be partially aminated by reacting its carboxyl group with compounds such as diamine, triamine and the polyamine. Adoptable diamines are ethylenediamine and hydrazides such as adipodihydrazide. Reaction of these amino compounds with carboxylic acid is by way of addition reaction with carbodiimide. In such occasion, adoptable is the degree of amination in a range of 0-100 mol/mol %. In same manner with blockage of amino groups, percentage of remaining carboxyl groups is preferably in a range of 50-99 mol %, more preferably in a range of 60-97 mol %, in each of which remaining percentage is for aminated carboxylic groups. For example, polyacrylic acid having average molecular weights of 1000-3,000,000, or 1000-10,000 in particular, is used; and 1-50 mol % of, preferably 3-40 mol % of, carboxyl groups of the polyacrylic acid are blocked with amines and carbodiimides such as ethylenediamine dihydrazide, or the like. Cryopreservation liquid according to the invention may also contain 0.3-15 w/w %, or 0.1-50 w/w % in particular, of conventional cryoprotectant materials such as DMSO, glycerol, ethylene glycol, trehalose or sucrose. Because cells are subject to damages caused by the oxidation stress during freezing and thawing, the addition of anti-oxidants to the cryoprotectant is expected to improve its preserving effects. For examples, anti-oxidants such as catalase, peroxidase, superoxide dismutase, vitamin E, vitamin C, polyphenols such as epigallocatechin gallate or glutathione may be used.

The osmotic pressure of the cryopreservation agent according to the invention is 200-1000 mOsm/kg, more preferably is 300-700 mOsm/kg, and further preferably 400-600 mOsm/kg. The cryopreservation agent according to the invention is applicable to the preservation of not only cells but also tissues. Examples of such cells and tissues to be cryopreserved by the cryopreservation agent are cultured cell lines, fertilized eggs of animal and human origin. Further examples are sperm cells, embryonic stem cells, IFS cells, mesenchymal stem cells, haemopoietic stem cells, neuronal stem cells, umbilical cord blood stem cells, hepatocytes, nerve cells, cardiomyocytes, vascular endothelial cells, vascular smooth muscle cells and blood cells. Not only animal or human cells but also plant cells can be included. Tissues and organs that are able to be preserved by the cryopreservation agent according to this invention are skins, nerves, blood vessels, cartilages, cornea, livers, kidneys, hearts and pancreatic islets.

An interesting aspect of the present invention is the ability to adjust the pH from the preferred range of 7.4 to greater or lesser amounts. This allows the electro field charge to be adjusted greater or lower as a tailored means of increasing or decreasing the predetermined time for the bonding shroud to be metabolized. Alternatively, the mixture and the protectant can be diluted prior to implantation with sterile water or saline or host blood to thin the protectant coating to shorten the time to be metabolized if so desired. In any event, the present invention insures no rinsing or separation of the protectant from the cells is required insuring much higher survivability of the donor mixture.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A freeze-dried composition consisting of:
    a mixture of biologic material derived from bone marrow, the mixture being a mechanically selected biologic material having non-whole cellular components including vesicular components and active and inactive components of biological activity, cell fragments, cellular excretions, cellular derivatives, and extracellular components, or combinations of the non-whole cellular components and whole cells, wherein the mixture is compatible with biologic function;
    a volume of a polyampholyte protectant, the polyampholyte protectant is a liquid of a polyamine polymer compound of carboxylated poly-lysine which is intermixed with the mixture of biologic material; and
    wherein the polyampholyte protectant forms a three-dimensional bonding shroud externally enveloping each of the non-whole cellular components, and each of the whole cells, if any, of the mixture of biologic material, wherein the mixture of biological material enveloped in the three dimensional bonding shroud of polyampholyte protectant when intermixed is preserved by freeze-drying and configured as a freeze dried composition consisting of only the mixture of biologic material and the polyampholyte protectant, configured for direct implantation when rehydrated in the absence of any washing or rinsing of the freeze-dried composition.

2. The freeze-dried composition of claim 1 wherein the bonding shroud deters attachment to other cells for a pre-determine time.

3. The freeze-dried composition of claim 1 wherein the bonding shroud buffers inflammation.

4. The freeze-dried composition of claim 1 wherein the bonding shroud retards or reduces premature differentiation of the whole cells of the mixture.

5. The freeze-dried composition of claim 1 wherein the bonding shroud sustains regenerative potential and biologic function of the mixture during preservation and implantation.

6. The freeze-dried composition of claim 1 wherein the bonding shroud is configured to be metabolized after implantation after a predetermined time.

7. The freeze-dried composition of claim 6 wherein the predetermined time is three or more days.

8. The freeze-dried composition of claim 7 wherein the predetermined time is up to six days.

9. The freeze-dried composition of claim 1 wherein the three-dimensional bonding shroud forms a spherical shell about each whole cell.

10. The freeze-dried composition of claim 1 wherein the polyampholyte protectant is a cryoprotectant.

11. The freeze-dried composition of claim 10 wherein the polyampholyte protectant forms a strong hydrophilic characteristic of the bonding shroud to protect the cell membrane external of the whole cells.

12. The freeze-dried composition of claim 1 wherein the biological composition is predisposed to demonstrate or support elaboration of active volume or spatial geometry consistent in morphology with that of endogenous bone.

13. The freeze-dried composition of claim 1 wherein the biological composition extends regenerative resonance that compliments or mimics tissue complexity.

14. The freeze-dried composition of claim 13 wherein the regenerative resonance occurs in the presence or absence of a refractory response.

15. The freeze-dried composition of claim 1 wherein the mixture which is derived from bone marrow of a cadaver has separation-enhanced non-whole cell fractions vitality including one or more of the following: separating the fractions from cells heightens their vitality, reversing "arrest" of donors, accentuating responsive molecular coupling, matrix guarding in neutralizing inflammation or providing a basis for metabolic satience by balancing stimulus for repair.

16. The freeze-dried composition of claim 1 wherein the protectant is a cryoprotectant polyampholyte of carboxylated poly-lysine and the volume of the polyampholyte protectant intermixed with the mixture of biologic material is freeze-dried.

17. The freeze-dried composition of claim 16 wherein the composition is maintained at ambient temperature prior to freeze drying.

18. The freeze-dried composition of claim 1 wherein the mixture creates a physical or electrical or chemical gradient or combination thereof for tissue regeneration.

19. The freeze-dried composition of claim 18 wherein the gradient has a physical characteristic such as modulus or topography.

20. The biological composition of claim 18 wherein the gradient has a chemical characteristic such as spatially changing compositions of density or species of functional molecules.

21. The biological composition of claim 18 wherein the gradient has an electrical characteristic such as charge based or pH based.

22. The freeze-dried composition of claim 1 can be organelle fragments.

23. The freeze-dried composition of claim 1 wherein active and inactive components of biological activity can be extants of the human metabolome.

24. A freeze-dried composition consisting of:
a mixture of biologic material derived from bone marrow, the mixture being a mechanically selected biologic material having a select number of non-whole cell fractions including one or more of exosomes, secretomes, transcriptosomes, proteasomes, membrane rafts, lipid rafts, non-whole cellular components including vesicular components and active and inactive components of biological activity, cell fragments, cellular excretions, cellular derivatives, and extracellular components, or combinations of the non-whole cellular components and whole cells, wherein the mixture is compatible with biologic function;
a volume of a polyampholyte protectant, the polyampholyte protectant is a liquid of a polyamine polymer compound of carboxylated poly-lysine which is intermixed with the mixture of biologic material; and
wherein the polyampholyte protectant forms a three-dimensional bonding shroud externally enveloping each of the non-whole cellular components, and each of the whole cells, if any, of the mixture of biologic material, wherein the mixture of biological material enveloped in the three dimensional bonding shroud of polyampholyte protectant when intermixed is preserved by freeze-drying and configured as a freeze dried composition consisting of only the mixture of biologic material and the polyampholyte protectant, configured for direct implantation when rehydrated in the absence of any washing or rinsing of the freeze-dried composition.

25. The freeze-dried composition of claim 24 wherein the combination of non-whole cell components with a select number of the non-whole cell fractions sustains pluripotency in both graft or host cells or combinations thereof.

26. The freeze-dried composition of claim 25 wherein the select number of the non-whole cell fractions upon grafting sustains pluripotency in graft or host cells or combinations thereof in the recipient.

27. A freeze-dried composition intermixed with a polyampholyte protectant for direct implantation consisting of: a mixture of biologic material derived from bone marrow, the mixture being a mechanically selected biologic material having non-whole cellular components including vesicular components and active and inactive components of biological activity, cell fragments, cellular excretions, cellular derivatives, and extracellular components, or combinations of the non-whole cellular components and whole cells, wherein the mixture is compatible with biologic function; a volume of a polyampholyte protectant, the polyampholyte protectant is a liquid of a polyamine polymer compound of carboxylated poly-lysine which is intermixed with the mixture of biologic material; and wherein the polyampholyte protectant forms a three-dimensional bonding shroud externally enveloping each of the non-whole cellular components, and each of the whole cells, if any, of the mixture of biologic material, wherein the mixture of biological material enveloped in the three dimensional bonding shroud of polyampholyte protectant when intermixed is preserved by freeze-drying and configured as a freeze-dried composition, configured for direct implantation when rehydrated in the absence of any washing or rinsing of the freeze-dried composition, wherein the mixture in an unfrozen, non-freeze-dried state is treated in the protectant prior to freeze drying.

28. The freeze-dried composition of claim 27 wherein the protectant creates a physical or electrical or chemical gradient or combination thereof for tissue regeneration.

29. The freeze-dried composition of claim 28 wherein the gradient has a physical characteristic of modulus or topography such as charge density, field shape or cyto-taxic, cryo- or chemo-taxic tendencies.

30. The biological composition of claim 28 wherein the gradient has a chemical characteristic of spatially changing compositions of density or species of functional molecules, wherein the molecules can offer a fixed catalytic function as a co-factor.

31. The biological composition of claim 28 wherein the gradient has an electrical characteristic of charge based or pH based or electron affinities that confer metastability in biologic potential.

32. A freeze-dried composition consisting of a mixture of biologic material derived from bone marrow, the mixture being a mechanically selected biologic material having non-whole cellular components including vesicular components and active and inactive components of biological activity, cell fragments, cellular excretions, cellular derivatives, and extracellular components, or combinations of the non-whole cellular components and whole cells, wherein the mixture is compatible with biologic function; a volume of a polyampholyte protectant, the polyampholyte protectant is a liquid of a polyamine polymer compound of carboxylated poly-lysine which is intermixed with the mixture of biologic material; and wherein the polyampholyte protectant forms a three-dimensional bonding shroud externally enveloping each of the non-whole cellular components, and each of the whole cells, if any, of the mixture of biologic material, wherein the mixture of biological material enveloped in the three dimensional bonding shroud of polyampholyte protectant when intermixed is preserved by freeze-drying and configured as a freeze dried composition of the mixture of biologic material and the polyampholyte protectant, configured for direct implantation when rehydrated in the absence of any washing or rinsing of the freeze-dried composition, wherein said protectant is a 1-50 w/w % aqueous solution of at least one polyamine polymer compound comprised of at least one polymer of units having side-chain amino groups, said at least one polymer of units being selected from a group consisting of ε-poly-L-lysine, α-poly-L-lysine, poly-arginine, allylamine polymer and partially methoxy-carbonylated allylamine polymer; and 50-99 mol % of amino groups, other than those forming amino-acid-to-amino-acid linkages, of said at least one polymer compound is blocked with carboxylic anhydride to form pendant moieties, each of which is linked to main chain of the polymer via an amide linkage and essentially has a not-blocked carboxylic group.

33. The freeze-dried composition according to claim 32, wherein said protectant liquid is obtained by dissolving the at least one polyamine polymer compound in a physiological solution.

34. The freeze-dried composition according to claim 33, wherein the physiological solution is a saline, Dulbecco-modified eagle MEM culture medium (DMEM), or a culture medium for cells or tissues.

35. The freeze-dried composition according to claim 32, wherein said at least one polymer compound is ε-poly-L-lysine having number-average molecular weight in a range of 1000-20,000.

36. The freeze-dried composition according to claim 32, wherein remaining side-chain amino groups or remaining side-chain and terminal amino groups of the at least one polymer compound are not blocked by covalent bonding.

* * * * *